United States Patent [19]
Settler et al.

[11] Patent Number: 5,690,680
[45] Date of Patent: Nov. 25, 1997

[54] ELECTRICAL BRIDGE FOR MEDICAL USE AND METHOD

[76] Inventors: Morris Settler, 590 Niagara Street, Winnipeg, Manitoba, Canada, R3N 0V4; Bert Settler, 723 Queenston Street, Winnipeg, Manitoba, Canada, R3N 0X8

[21] Appl. No.: 602,906

[22] Filed: Feb. 16, 1996

[30] Foreign Application Priority Data

Feb. 21, 1995 [GB] United Kingdom .................. 9503438

[51] Int. Cl.$^6$ ............................. A61B 5/0402; A61N 1/08
[52] U.S. Cl. ............................. 607/2; 607/115; 128/73 A
[58] Field of Search ............................. 607/113, 2, 115; 128/632, 763, 760, 637, 764, 656, 653.2, 653.4, 654, 734

[56] References Cited

U.S. PATENT DOCUMENTS 5,480,420  1/1996  Hoegnelid et al. .................. 607/116

Primary Examiner—Scott M. Getzow
Attorney, Agent, or Firm—Pascal & Associates

[57] ABSTRACT

An electrical bridge for communicating signals to or from an organ or a patient comprising a non-porous, non-metallic, flexible tubular duct, an ionically conductive liquid contained in the duct for transmitting electrical signals by ion transfer and a non-metallic conductive plug at an end of the duct for electrically connecting to the organ or patient.

23 Claims, 3 Drawing Sheets

ELECTRICAL BRIDGE FOR MEDICAL USE AND METHOD

FIELD OF THE INVENTION

This invention relates to the field of medical instrumentation, and in particular to a bridge that can be used for electrical monitoring or electrical stimulation of a biological entity.

BACKGROUND TO THE INVENTION

Electrical monitoring or stimulation of a biological entity such as an organ has been effected in the past by the use of metal conductors which are in contact with the biological entity (to be referred to generically as an organ in this specification). While it has been important that the metal conductors are constituted by a material that can be tolerated by the organ (or body through which the conductor passes), a major problem arises when the conductors are located in the environment of a high intensity moving magnetic field, e.g. an electromagnetic field such as is generated by a magnetic resonance imaging (MRI) machine. The moving high intensity electromagnetic field generates electric currents in the metal conductors, which can adversely affect normal operation of the organ which it touches, and can change or otherwise affect the signals picked up by the MRI machine, resulting in poor or incorrect interpretation of the form of the organ, hiding of formations, and/or incorrect diagnosis of a problem associated with the organ.

An example of the above is an attempt to use an MRI machine to observe operation of a heart the beating of which is timed by means of a pacemaker connected to the heart by metal wires.

SUMMARY OF THE INVENTION

The present invention is a bridge that can be used to carry current to or from an organ, such as a heart, without the use of metal wires. We have found that the present invention is substantially unaffected by the moving electromagnetic field generated in an MRI machine, and has little or no effect on the resulting signals picked up by the MRI machine. Accordingly the invention can be used to pace the heart or to monitor the heart in the presence of such electromagnetic fields. In addition, the invention can be used for other purposes, such as for electrocardiogram monitoring, electroencephalogram monitoring, etc., whether or not an electromagnetic field is present.

A novel portable connection capsule has been invented which can be used to connect the bridge to monitoring apparatus.

In accordance with an embodiment of the invention, an electrical bridge or communicating signals to or from an organ or a patient is comprised of a non-porous, non-metallic, flexible tubular duct, an ionically conductive liquid contained in the duct for transmitting electrical signals ion transfer and a non-metallic conductive plug at an end of the duct for electrically connecting to the organ or patient.

In accordance with another embodiment, a method of communicating signals to or from an organ or a patient within the environment of an MRI machine is comprised of providing a non-porous, non-metallic, flexible tubular duct filled with an ionically conductive liquid for transmitting electrical signals by ion transfer, and providing a non-metallic conductive plug at an end of the duct electrically connected to the organ or patient.

In accordance with another embodiment, a method of communicating signals to or from an organ or a patient within the environment of an MIR machine is comprised of providing a non-porous, non-metallic, flexible tubular duct filled with an ionically conductive liquid for transmitting electrical signals by ion transfer, providing an electrical connection between the patient and the liquid and providing an electrical connection from the liquid to a metal conductor by immersing the end of the duct and the conductor into an ionically conductive liquid or gel bath.

In accordance with another embodiment, a method of applying signals to an organ is comprised of connecting a pair of ionic conducting bridges to the organ, each bridge being comprised of an insulating tube filled with a liquid salt solution, a porous plug at one end of each tube touching the organ, immersing opposite ends of the tubes in separate reservoirs containing liquid salt solutions, immersing one end of a pair of metal wires into respective ones of the reservoirs, and connecting the other ends of the wires to an electric generator for generating the signals.

In accordance with another embodiment, a method of monitoring signals generated in an organ is comprised of connecting at least a pair of ionic conducting bridges to a body containing the organ, each bridge being comprised of an insulating tube filled with a liquid salt solution, a porous plug at one end of each tube touching the body, immersing opposite ends of the tubes in separate reservoirs containing liquid salt solutions, immersing one end of each wire of a corresponding at least a pair of metal wires into respective ones of the reservoirs, and connecting the other ends of the wires to an electrical signal monitoring device.

In accordance with another embodiment, an ionic conductor is comprised of a long tube filled with thixotropic gel comprising a salt solution, a porous plug closing one end of the tube, a non-porous plug closing the other end of the tube, and a metal wire extending through the non-porous plug into the gel and having a free end outside the non-porous plug.

BRIEF INTRODUCTION TO THE DRAWINGS

A better understanding of the invention will be obtained by considering the detailed description below, with reference to the following drawings, in which.

DETAILED DESCRIPTION OF PREFERRED EMBODIMENTS

Figure 1:
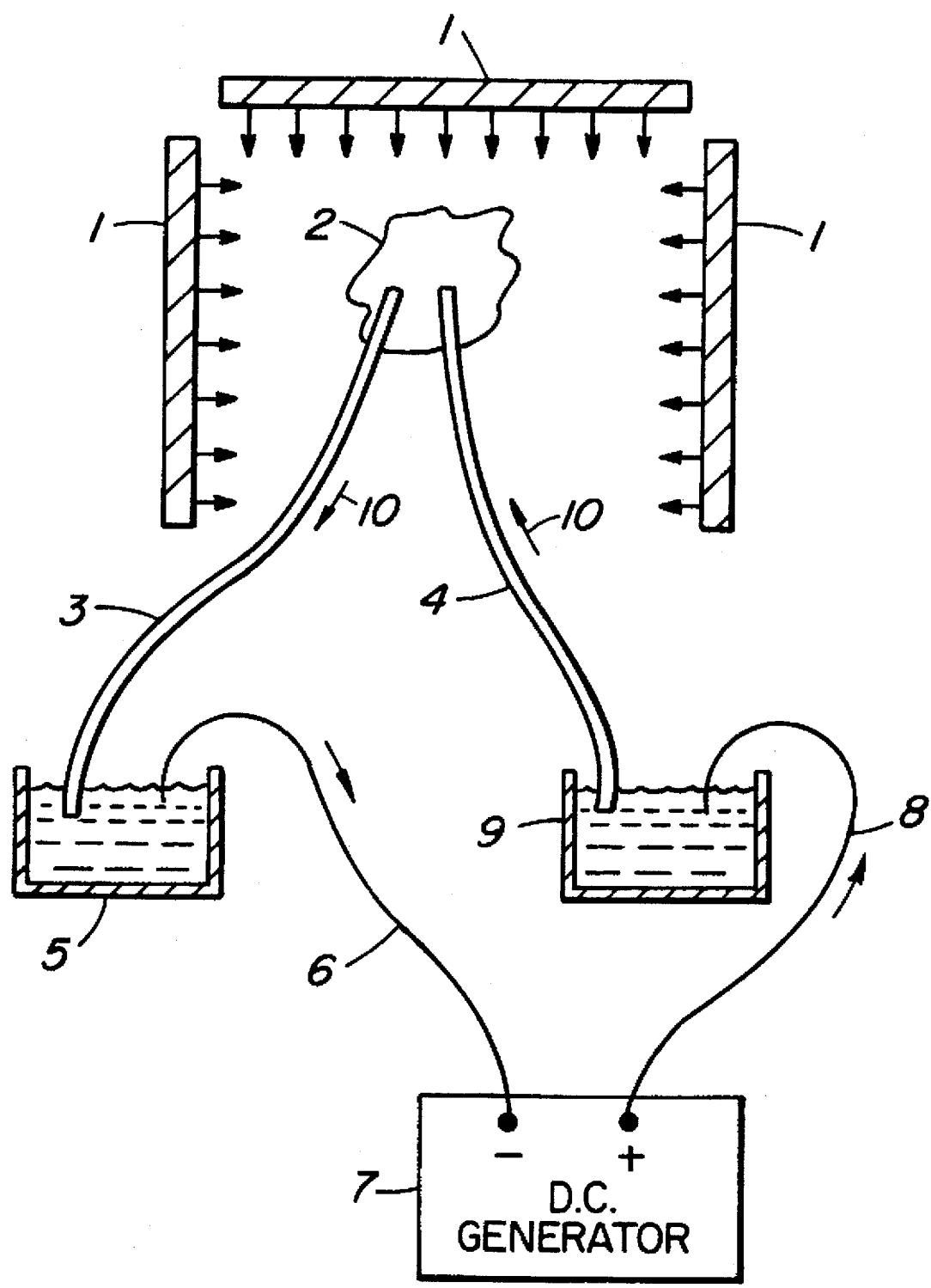
FIG. 1 is a schematic drawing of a first embodiment of the invention in use.

FIG. 1 shows an excised heart 2 which is to be paced in an MRI spectroscopy environment, in order to obtain scientific or pharmacological determinations using MRI spectroscopy. Since MRI exhibits very high electromagnetic fields as well as very high radio frequencies, it is difficult to obtain good signal to noise ratios, to determine the data required. Since pacing is done with convention D.C. signal generators, the current and voltage delivered, to pace the heart, requires leads to and from the heart 2 that pass through the MRI electromagnetic fields. Platinum or other conventional metal leads present a major problem in the high radio frequency fields. In the high electromagnetic environment of the MRI, the signal to noise ratio is very low and it is difficult to obtain a signal carrying the information required.

Two ion salt bridges 3 and 4 are used which in effect are wireless and metalless. When they are used for pacing heart 2, the signal to noise ratios have been found to be sufficiently high that pharmacological or scientific data can be obtained. The heart 2 is paced by D.C. voltage and current provided from generator 7 via reservoirs 5 and 9 which form bridge junctions. Metal lead wires 6 and 8 are connected between generator 7 and reservoirs 5 and 9 and ion bridges 3 and 4 are connected between reservoirs 5 and 9 and the heart 2 to be paced. A current path thus is provided from generator 7 to reservoir 9 via lead wire 8, from reservoir 9 via bridge 4 to heart 2, from heart 2 via bridge 3 to reservoir 5 and via metal lead wire 6 to generator 7.

The bridges 3 and 4 are preferably 48" or longer so that the reservoirs 5 and 9 and generator 7 are out of range of the radio frequency fields and magnetic effects of the MRI machine.

MRI measurements are made, which is made possible because the bridges 3 and 4 are wireless and metalless. The bridges are preferably made of 2 mm (but can be smaller or larger) polyethylene tubing, filled with a thixotropic gel of 3.6 molar KCL. Inside the full length of the 48 inches or more is a saturated cotton thread. The gel and cotton thread fill the tubing to ensure against bubbles, air locks, dry out and crystallization.

Both ends of the ion bridges 3 and 4 are terminated in two tapered fibrous (pulp) porous junctions with the cotton thread in contact with each pulp junction. The pulp junctions and the cotton thread should be saturated in a 4 molar KCL before production is undertaken. When not in use the ion bridges should be stored in 4 molar KCL solution.

The above-described ion bridges conduct the ions which have been found to be unaffected by the R.F. Reservoirs 5 and 9 which act as intermediaries (junctions) between the D.C. generator 7 and leads 6 and 8. Ion abridges 3 and 4 continue ion and thus current flow to the heart being paced, without being substantially affected by, or affecting the MRI electromagnetic field.

The ion bridges 3 and 4 can be made longer, if more distance is needed to place the reservoir leads 6 and 8 out of the influence of the MRI electromagnetic field. The gel composition and cross section of the ion bridge can be altered to increase current flow just as one would change the wire size and length to do the same.

The ion bridges 3 and 4 and reservoirs 5 and 9 are inexpensive to fabricate, can be sterilized, are storable and are reusable.

Figure 2:
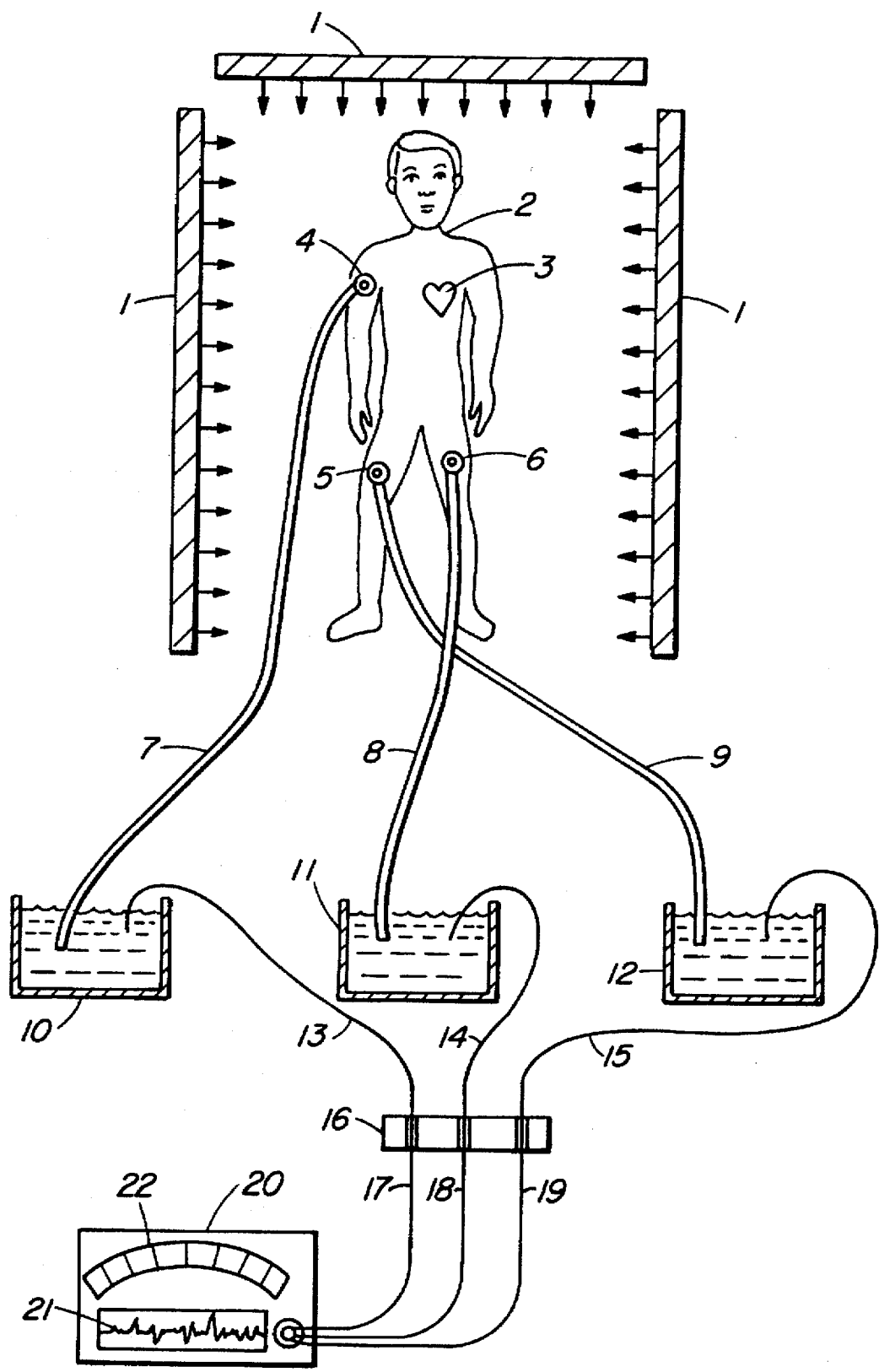
FIG. 2 is a schematic drawing of a second embodiment of the invention in use.

FIG. 2 shows a patient 2 in an MRI machine, subjected to a high electromagnetic field. In the conventional method the patient is to be connected to an electrocardiogram (E.K.G.). However use of a conventional EKG monitor, lead wires, and monitoring electrodes, is difficult or impossible since the metal in the lead wires and electrodes make the signal to noise ratio too low as a result of the high R.F. and high electromagnetic field of the MRI machine. The present invention overcomes this problem by providing a wireless, metalless bridge in place of the metal leads, and which does not reduce the signal to noise ratio. This permits the monitoring of a high risk, critically ill patient during an MRI procedure.

The procedure uses, for example, three bridges and connectors to obtain an acceptable E.K.G. trace and heart rate.

A conventional E.K.G. machine 20 is used that displays e.g. trace 21 and heart rate 22. The E.K.G. cables 17, 18, 19 are typically connected to a junction block 16. Three metal leads 13, 14, 15 connect to block 16 in order to connect to corresponding leads 17, 18 and 19 respectively. The other ends of leads 13, 14, 15 are dropped into reservoirs 10, 11 and 12. Reservoirs 10, 11 and 12 are located outside of the environment of the MRI electromagnetic field as well as the monitor 20, cables 17, 18, 19, 13, 14, 15 and block 16.

The reservoirs 10, 11 and 12 contain a 4 molar KCL solution as in the first embodiment of the invention described with reference to FIG. 1. Reservoirs 10, 11 and 12 interface metal leads 13, 14, 15 with ion bridges 7, 8 and 9. Ion bridges 7, 8 and 9 are physiological ion salt bridges that carry signals from the patient 2 to the monitor 20 via reservoirs 10, 11, 12 and leads 13, 14, 15, 17, 18, 19.

The leads 7, 8, 9 are preferably about 48" long, are metalless and wireless, conduct ions and are substantially unaffected by the high radio frequency fields and the high electromagnetic fields of the MRI machine 1. The construction and design of the ion bridges are similar to that described with reference to the embodiment of FIG. 1.

The ion bridges 7, 8 and 9 must be connected to the patient 2 to carry the signal to monitor 20. The connection is effected by electrodes 4, 5 and 6. These are preferably comprised of a 2" or small foam or tape adhesive, to which is attached a 2 cm plastic (biocompatible) cup or well to hold a column of 3.6 molar KCL gel (the same gel as in the ion bridge). A small recess is cut in the plastic well to accept and hold a corresponding ion bridges 7, 8 or 9. Electrodes 4, 5 and 6 and ion bridges 7, 8 and 9 can be adhered to the patient by the acrylic adhesiveness of the foam or tape pad. The monitoring electrodes 4, 5 and 6 can be for one time use, and disposable. A syringe, containing the 3.6 molar KCL gel can be supplied with a pack of the electrodes 4, 5 and 6 and used to fill each well.

As with the fist embodiment, the 48" or longer length of the bridges 7, 8, 9 make it possible for the reservoirs 10, 11, 12, cables 13, 14, 15, 17, 18, 19 and block 16 and monitor 20 be out of the environment of the MRI electromagnetic and radio frequency fields effectively monitor the patient.

Figure 3:
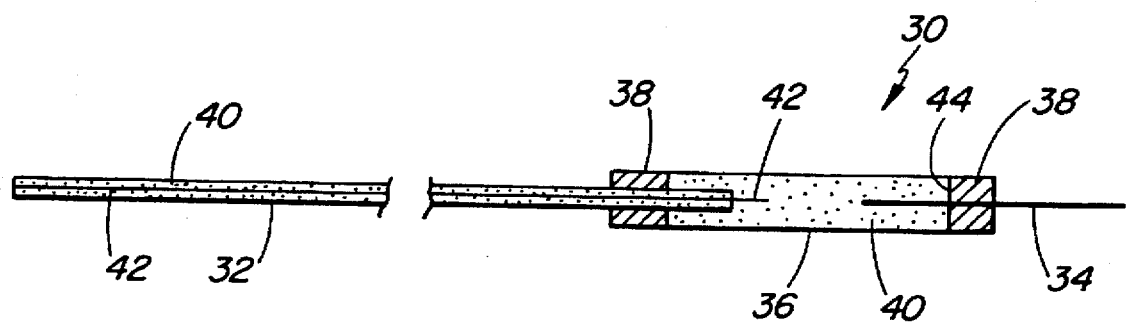
FIG. 3 is a cross-section of a third embodiment of the invention, a bridge connection capsule which can form part of the embodiments of FIGS. 2 or 3.

FIG. 3 illustrates the cross-section of another form of the liquid connection reservoirs 10, 11 and 12 described above, in the form of a capsule 30. The arrangement is provided in order to be able to monitor or pace an animal or human heart or any other organ in an MRI or NMRI spectroscopy environment, as described above, using the wireless, non-metallic ion bridge described herein.

The capsule 30 can replace the liquid junctions 5, 9, 10, 11, 12 since the latter junctions have limitations due to size, bulk, and spilling, especially when used in an NMRI nuclear magnetic resonance imaging, or spectroscopy environment. The capsule or connector comprises a bridge as will be described and a short metal (e.g. copper) wire lead 7. The medium for conducting the ion flow in the bridge is the same gel used in the earlier described ion KCL salt bridges, which results in less chance of developing junction potentials.

Each capsule 30 is comprised of a preferably 10 foot to 13 foot or longer ion KCL salt bridge 32 extending from one end. A metal (e.g. copper) very short lead 34 extends from the other end.

The capsule 30 in the drawing is an apparatus of transferring electron flow from an ion KCL wireless nonmetallic bridge or conductor to a short metal conductor. The very short metal conductor has been determined not to affect the MRI signal at the MRI end.

For E.C.G., or E.E.G. monitoring in an MRI environment, the embodiment of FIG. 3 can be used. The ion bridge 32 is connected to the subject or patient for each of 3 leads or 5 leads of the E.C.G. or E.E.G. The length allows the capsule and wire 34 to be located out of the NMRI environment. Wire 34 connects to the instrument doing the measurement.

To monitor pH in an organ in an MRI environment, a 10 to 13 foot or longer ion bridge terminating in capsule 30 can be used with the short wire 34 connected to the pH electrode or other ion electrodes. The other end or a second capsule are located out of the NMRI environment, with wire 34 connected to the instrument doing the recording.

The capsule 30 in FIG. 3 is preferably comprised of a 2 inch long barrel of 1 c.c. syringe 36, forming a cylindrical tube, and two rubber bushings 38 each closing a correspond end of the tube. The tube is filled with thixotropic gel 40 (same as the gel in bridge 32). An ion KCL bridge 32 which is preferably 10 to 13 feet or longer as previously described, includes a tubular duct, gel 40 and cotton strand 42 or yarn with the cotton strand or yarn projecting outward from the end of a plug of the duct at the remote end.

A short copper wire 34, generally less than 2 inches long and 0.25 diameter extends from the gel 40 outwardly through bushing 38.

Preferably a fibrous strain relief 44 is used for wire 34. The cotton thread extends into the cylinder 36.

The capsule #1 is light, compact, and has been found to be easier to use and is more rugged than the earlier described liquid reservoir system of converting or transferring the electron flow from the ion KCL gel bridge to a very short copper wire.

Applications of the above described invention are for example to pace a patient's or animal's heart, be it pig, toad, rat or other hearts and organs, during an MRI spectroscopy procedure using two physiological ion salt bridges and two reservoirs filled with 4 molar KCL solution, to monitor a patient's or animal's heart during an MRI procedure using for example three physiological ion salt bridges and three reservoirs filled with 4 molar KCL solution. The reservoirs can be generally as described with reference to FIGS. 1 or 2, or as described with reference to FIG. 3.

A person understanding this invention may now conceive of alternative structures and embodiments or variations of the above. All of those which fall within the scope of the claims appended hereto are considered to be part of the present invention.

We claim:

1. A method of applying signals to an organ comprising connecting a pair of ionic conducting bridges to the organ, each bridge being comprised of an insulating tube filled with a liquid salt solution, a porous plug at one end of each tube touching the organ, immersing opposite ends of the tubes in separate reservoirs containing liquid salt solutions, immersing one end of a pair of metal wires into respective ones of the reservoirs, and connecting the other ends of the wires to an electric generator for generating said signals.

2. A method of monitoring signals generated in an organ comprising connecting at least a pair of ionic conducting bridges to a body containing the organ, each bridge being comprised of an insulating tube filled with a liquid salt solution, a porous plug at one end of each tube touching the body, immersing opposite ends of the tubes in separate reservoirs containing liquid salt solutions, immersing one end of each wire of a corresponding at least a pair of metal wires into respective ones of the reservoirs, and connecting the other ends of the wires to an electrical signal monitoring device.

3. An ionic conductor comprising a long tube filled with thixotropic gel comprising a salt solution, a porous plug closing one end of the tube, a non-porous plug closing the other end of the tube, and a metal wire extending through the non-porous plug into the gel and having a free end outside the non-porous plug.

4. An ionic conductor as defined in claim 3 further including a cotton thread contained within and extending substantially the length of the tube into the vicinity of the wire.

5. An ionic conductor as defined in claim 4 in which the thread extends through the porous plug.

6. An ionic conductor as defined in claim 4 in which said other end of the tube is in the form of a cylinder closed at both ends and having a diameter wider than a narrower diameter of the of the remainder of the tube, the narrower diameter remainder of the tube extending into the cylinder, and the wire extending from outside to inside the cylinder, the cylinder being filled with said gel.

7. An ionic conductor as defined in claim 4 in which the gel in the narrower diameter remainder of the tube has the viscosity of liquid.

8. An electrical bridge for communicating signals to or from an organ or a patient comprising a non-porous, non-metallic, flexible tubular duct, an ionically conductive liquid contained in the duct for transmitting electrical signals by ion transfer and a non-metallic porous conductive plug at an end of the duct for electrically connecting to the organ or patient, wherein the duct is electrically connected to a metal cable in a junction, the junction comprising a container of ionically conductive liquid or gel into which an opposed and open end of the duct is inserted with one end of the metal cable.

9. The bridge as defined in claim 8 wherein the plug is fibrous.

10. The bridge as defined in claim 8 wherein the plug includes interstices impregnated with the liquid for allowing the liquid to provide conductivity through the plug, the plug preventing bleeding or leeching of the liquid.

11. The bridge as defined in claim 8 wherein the duct includes a continuous non-metallic thread extending longitudinally of the duct within the liquid.

12. The bridge as defined in claim 11 wherein the thread is fibrous.

13. The bridge as defined in claim 11 wherein the thread is made of cotton.

14. The bridge as defined in claim 8 wherein the container comprises a closed capsule containing a gel the same as or compatible with the liquid or gel in the tubular duct, wherein the metal cable or wire is sufficiently short to avoid interference from fields generated by an MRI machine, and wherein the tubule duct projects through one end of the capsule and the wire projects through the other end of the capsule.

15. The bridge as defined in claim 14, wherein the gel is a 4 molar KC1 solution.

16. The bridge as defined in claim 8 wherein the bridge is used in the environment of an MRI machine.

17. The bridge as defined in claim 8 wherein the liquid is a 4 molar KCl solution.

18. A method transmitting electrical signals to or from an organ or a patient by means of an electrical bridge within the moving electromagnetic field of an MRI machine comprising providing a non-porous, non-metallic flexible tubular duct filled with a liquid fro transmitting electrical signals by ion transfer, and providing a non-metallic porous conductive plug at an end of the duct electrically connected to the organ or patient, wherein the liquid is a 4 molar KCl solution.

19. A method of transmitting electrical signals to or from an organ or a patient by means of an electrical bridge within the moving electromagnetic field of an MRI machine comprising providing a non-porous, non-metallic flexible tubular duct filled with an ionically conductive liquid for transmitting electrical signals by ion transfer, providing an electrical connection between the organ or patient and the liquid and providing an electrical connection from the liquid to a metal conductor by immersing the end of the duct and the conductor into an ionically conductive liquid or gel bath.

20. A method as defined in claim 19 wherein the liquid is a 4 molar KCl solution.

21. A method as defined in claim 19 wherein electrical connection between the patient and the liquid is obtained by containing the liquid within a cup or well attached to the duct and by an adhesive means to the patient.

22. An electrical bridge for communicating signals to or from a patient comprising a non-porous, non-metallic, flexible tubular duct, an ionically conductive liquid contained in the duct for transmitting electrical signals by ion transfer and means at an end of the duct for providing an electrical connection between the patient and the liquid, wherein the duct is connected to a metal cable in a junction, the junction comprising a container of ionically conductive liquid or gel into which an opposed and open end of the duct is inserted with one end of the metal cable, and wherein the means for providing an electrical connection between the patient and the liquid comprises a cup or well attached to the flexible duct, adapted to be attached by an adhesive means to the patient, and containing the ionically conducive liquid in contact with the patient.

23. A bridge as defined in claim 22 wherein the adhesive means comprises an adhesive foam pad or tape.

* * * * *